United States Patent [19]

Cherksey et al.

[11] Patent Number: 5,242,947
[45] Date of Patent: Sep. 7, 1993

[54] USE OF POLYAMINES AS IONIC-CHANNEL REGULATING AGENTS

[75] Inventors: Bruce D. Cherksey, Hoboken, N.J.; Rodolfo R. Llinas; Mutsuyuki Sugimori, both of New York, N.Y.

[73] Assignee: New York University, New York, N.Y.

[21] Appl. No.: 817,900

[22] Filed: Jan. 3, 1992

Related U.S. Application Data

[63] Continuation-in-part of Ser. No. 219,105, Jul. 14, 1988, Pat. No. 4,950,739, and Ser. No. 375,776, Jul. 3, 1989, abandoned, said Ser. No. 219,105, is a continuation-in-part of Ser. No. 154,845, Feb. 10, 1988, abandoned.

[51] Int. Cl.$^5$ .................. A61K 31/16; A61K 31/155; C07C 257/14; C07C 257/20
[52] U.S. Cl. ................................. 514/628; 514/634; 564/197; 564/240
[58] Field of Search ................ 564/197, 240; 514/626, 514/634

[56] References Cited

U.S. PATENT DOCUMENTS 3,574,747  4/1971  Denning ............................. 564/197

FOREIGN PATENT DOCUMENTS 2113089  8/1983  United Kingdom .

OTHER PUBLICATIONS

Meadows et al., *Toxicon*, 8:311–312, 1970.
Gregson, R. P., et al., *Comp. Biochem. Physiol.*, 74C (1):125–132, 1983.
Scheumack, D. D., et al., *Febs. Letters*, 191 (1):154–156, 1985.
Jackson, H., et al., *Soc. Neurosci. Abstr.* 185 p. 107, 32.17, 1985.
Curtis, B. M., et al., *Biochem.* 25:3077–3083, 1986.
Adams, M. E., et al., *Insect Neurophysiol. Pap. Int. Conf. Second*, pp. 397–400, 1986.
Jackson, H., et al., "Presynaptic Blockade of Transmission by a Potent, Long-Lasting Toxin from *A. aperta*", *Soc. Neurosci. Abstr.* 12, p. 730, 197.4, 1986.
Jackson, H., et al., *In Excitatory Amino Acid Transmission*, (Alan R. Liss, Inc.), pp. 51–54, 1987.
Miller, R. J., *Science*, 235:46,52 1987.
Bowers, C. W., et al., *PNAS (USA)*, 84:3506–3510, 1987.
Sugimori, M., et al., *Soc. Neurosci Abstr.*, 13 p. 228, 69.1, 1987.
Kerr, L. M., et al., *Soc. Neurosci. Abstr.*, 13 p. 102,31.15, 1987.
Lai, F. A., et al, *Nature*, 331:315–319, 1988.
Spence, J, *Neurotoxins, Fundam. Clin. Adv.* (Int's Conf.), pp. 161–173, 1979.
Jackson, H., et al., *TINS*, 11:278–283, 1988.
Palade, "Drug Induced Ca$^{2+}$ Release from Isolated Sarcoplasmic Reticulum", *The Journal of Biological Chemistry*, 262, 1, 33, 37:13 pp. 6149–6154, May 5, 1987.
Llinas et al., "Blocking and isolation of a calcium channel from neurons in mammals and cephalopods utilizing a toxin fraction (FTX) from funnel-web spider poison", *Proc. Natl. Sci.*, 86:1689–1693, Mar., 1989.
Llinas et al, "Voltage–dependent Calcium Conductances in Mammalian Neurons, The P Channel", *Annuals New York Academy of Sciences*, 560:103–111, 1989.
M. Nitsu, et al., "Synthesis of a Series of Linear Pentaamines with Three and Four Methylene Chain Intervals", *Chem. Pharm. Bull.*, 34, 3:1032–1038, 1986.
M. Israel et al., "Synthesis of Aminoethyl Derivatives of Alpha–omega–alkylenediamines and Structure-activity Relationship for the Polyaminebovine Plasma Amine Oxidase System", *Journal of Medical Chemistry*, 14 (11):1042–1047, 1986.

*Primary Examiner*—Richard L. Raymond
*Attorney, Agent, or Firm*—Darby & Darby

[57] ABSTRACT

Methods for regulating cation transport across cellular membranes possessing cation channels are provided. The cell membrane possessing a specific ion channel is exposed to a non-aromatic polyamine compound having a lysine- or arginine-based moiety (or a guanidine moiety) coupled to a straight chain polyamine.

These polyamines as well as a method for regulating NMDA through a spermidine-like effect on NMDA receptors by exposing a cell membrane to selected polyamines are also provided.

23 Claims, 6 Drawing Sheets

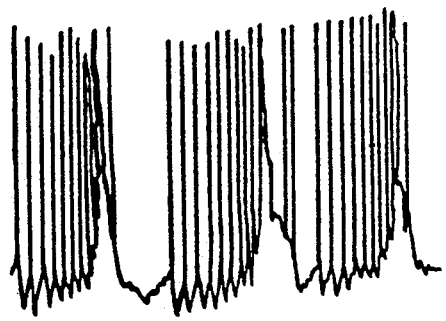
FIG. IA
FIG. IB 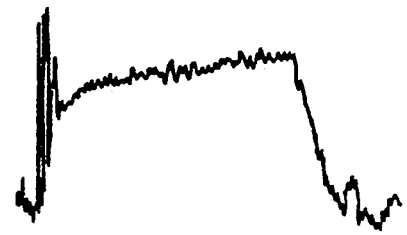
FIG. IC
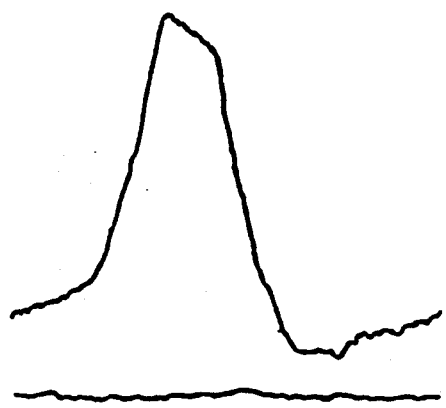
FIG. ID

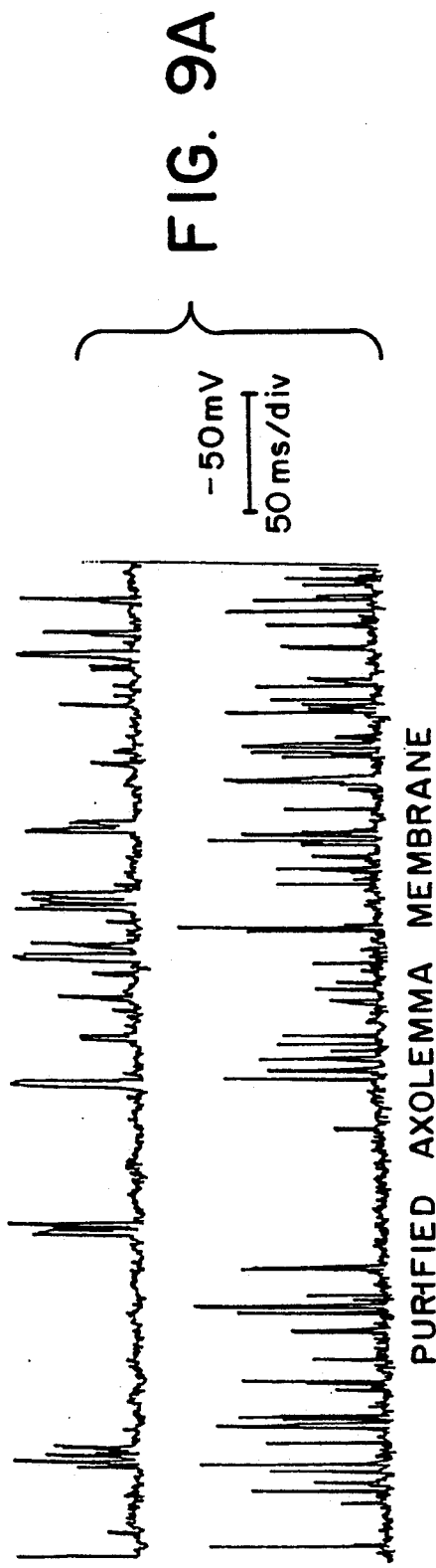
FIG. 9A
PURIFIED AXOLEMMA MEMBRANE
−50 mV
50 ms/div
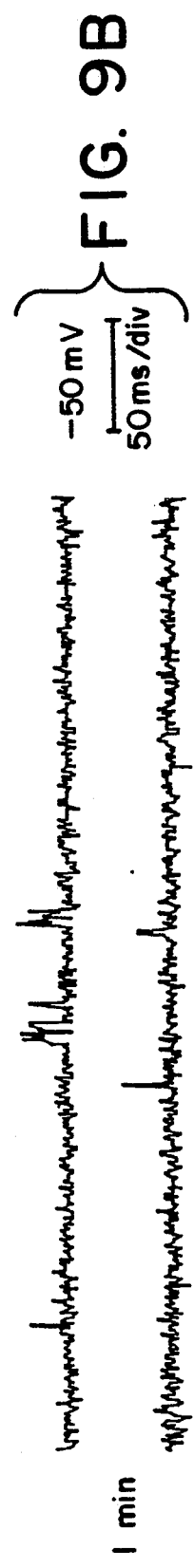
FIG. 9B
−50 mV
50 ms/div
FIG. 9C
1 min
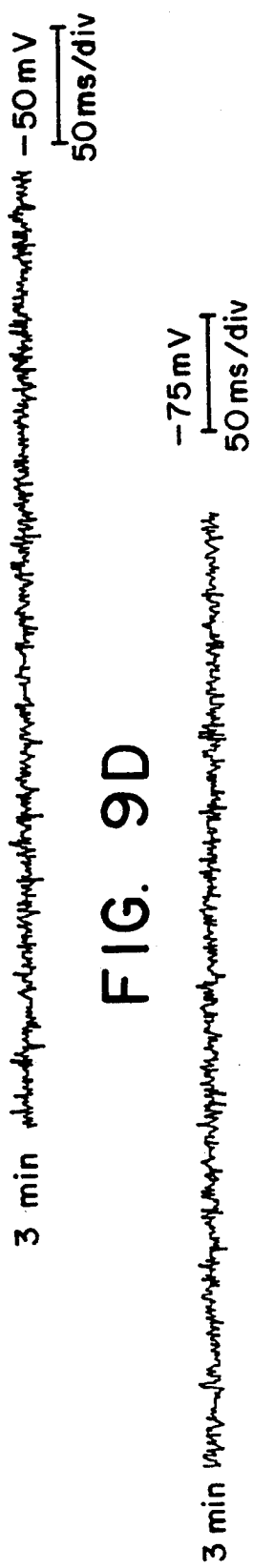
−50 mV
50 ms/div
3 min
FIG. 9D
−75 mV
50 ms/div
3 min

USE OF POLYAMINES AS IONIC-CHANNEL REGULATING AGENTS

This application is a continuation in part of (a) of U.S. patent application Ser. No. 219,105 filed Jul. 14, 1988, now U.S. Pat. No. 4,950,739, in turn a continuation-in-part of U.S. patent application Ser. No. 14,845 filed Feb. 10, 1988 (now abandoned); (b) PCT Application PCT/US89/00558 filed on Feb. 10, 1989, (c) U.S. application Ser. No. 375,776, filed Jul. 3, 1989, now abandoned, and (d) PCT/US90/03771, filed on Jul. 3, 1990. The United States Government has rights in this invention by virtue of Grant Nos. NS-13742 from the National Institute of Neurological and Communicative Disorders and Stroke, NIH EY-08002 from the National Eye Institute, U.S. Public Service, National Institutes of Health, AGE-A1PO1AG09480 from the National Institute on Aging, and AFOSR 89-0270 from the U.S. Air Force, Department of Defense.

FIELD OF THE INVENTION

This invention relates generally to the use of polyamine compounds as agents regulating ionic conductances in cellular membranes. These compounds have ω-spermidine-like effects on NMDA receptors and, as such, may act as NMDA regulators. Certain of these compounds also have separate and specific ion channel effects. These effects, in general, and particularly the ion channel effects, are believed to be of therapeutic value.

BACKGROUND OF THE INVENTION

Transport of charged particles across cell membranes is mediated (and in substantial part, regulated) by membrane proteins (including those referred to as "voltage-sensitive" or "voltage-dependent" channels as well as "ligand-gated" channels).

In this discussion the terms "channel" and "channel protein" are used interchangeably without implying that a channel must necessarily consist of a single protein, although channels that have been isolated are believed to be single proteins.

Most channel proteins mediate the transport of one ionic species with substantially higher specificity than transport of other ionic species. It is common to name various channels after the ion for which they are specific: thus, there are sodium channels, potassium channels, calcium channels, etc.

In turn, ionic channels specific for the transport of one cation, may be further divided into various subcategories or channel types, based on the way they interact in response to electrical and/or chemical (pharmacological) stimuli. Calcium channels in particular, which have been identified in a number of different cell types, including neurons, appear to have differences (as well as similarities) in morphology, properties and/or function. Other such differences have not been directly related to cell types; in fact, different types of channels are normally present in the same cell.

Historically, neuronal calcium conductances were first divided into two categories based on the driving force that activates them: the high-threshold calcium conductance (HTCC) and the low-threshold calcium conductance (LTCC). In central neurons, HTCC is more prominent in the dendrites and LTCC is more prominent in the soma or cell body. Later, neuronal calcium channels were grouped into three categories: the T-channels, which are believed to be responsible for LTCC; the N-channels, the conductance properties of which showed imperfect correspondence to HTCC; and the L-channels which are not commonly represented in central neurons but of which the conductance properties also showed correspondence to HTCC.

These three categories can be further distinguished by differences in pharmacological properties. The L-channels are dihydropyridine-sensitive, i.e. they are effectively blocked by dihydropyridines, such as nifedipine and nitrendipene, whereas the T- and N-channels are dihydropyridine-resistant. To a large extent, some T-channels resist blockage by cadmium ions; more importantly, some T-channels are specifically blocked by alcohols (especially octanol) at $10^{-4}$ M or lower concentrations. Finally, the N-channels are said to be blocked by omega-conotoxin, a toxin isolated from the venom of the marine snail *Conus geographicus*, to which the L- and T-channels are resistant. Miller, R. J. *Science*, 1987, 235: 46–52.

However, the calcium channels responsible for the HTCC (both the calcium-dependent plateau potential component and the dendritic spike component of the HTCC) in Purkinje cells are activated at $-50$ mV, and are dihydropyridine-insensitive and also omega-conotoxin-resistant. These channels are specifically blocked by a low-molecular weight blocking agent isolated from the venom of funnel-web spiders. Llinas et all, *Proc. Nat'l Acad. Sci. USA*, 1989, 86:1689–1695. Furthermore, the dihydropyridine- and conotoxin-resistant calcium channels appear to be absent from inferior olivary and thalamic neurons. These calcium channels have been called P-channels because they were first described in Purkinje cells. Llinas, et all, *Ann. N.Y. Acad. Sci.*, 1989, 560:103–111. P-type channels ave also been shown to exist in squid giant synapse and squid optic lobe.

Sodium and potassium channels are also of various types. See generally Hille, B. "Ionic Channels of Excitable Membranes," Sinauer Assoc. Inc., Sunderland, Mass., 1984.

Two main types of sodium channels are found in electrically excitable cells such as central neurons. One type of channel, responsible for the so-called "fast" sodium conductance, is specifically blocked by tetrodotoxin (TTX), a toxin isolated from puffer fish. A second type of sodium channel, responsible for the slow sodium current, is blocked by local anesthetic agents such as lidocaine. A distinctly different sodium channel is located in non-electrically excitable tissue such as epithelium, and is not blocked by TTX or the local anesthetics but is blocked by the diuretic amiloride.

The known blockers of $K^+$ channels include tetraethylammonium (TEA), aminopyridines and quinine.

Agents that block calcium channels with high affinity and/or specificity as well as agents that activate calcium channels are useful as reagents in electrophysiological research. Availability of such agents is essential for understanding calcium channel properties and function. Such agents are especially useful in the design of prototype drugs and in drug screening.

The prior art calcium-channel blocking agents do not satisfy this need for one or more of the following reasons:

(a) *Lack of Affinity for Particular Calcium Channels.* The P-channel in particular is resistant to: omega-conotoxin; dihydropyridine and its derivatives; and alcohols.

(b) *Lack of Specificity.* When developing substances that regulate a certain channel, specificity is a primary concern.

(c) *Unavailability in Large Amounts at Low Cost.* It would be desirable to identify channel regulating agents which could be synthesized conveniently and at low cost.

(d) *Lack of Knowledge of Blocking Agent Mode of Action.* The availability of blocking agents of different structure would help to elucidate the mechanism and to identify the site of blocking activity. This would in turn lead to design of improved blocking agents or of novel agents that had different calcium channel modulating properties, such as activation of calcium channels.

The calcium channel modulators of the present invention also have potential uses as prototypic drugs exhibiting anticonvulsant (e.g. anti-epileptic), anxiolytic, tranquilizing, anti-Alzheimer's, and/or memory-improving properties.

Analogous needs exist for substances that alter the ion-transport properties of other ionic channels, such as sodium or potassium channels, Such substances also find therapeutic uses such as:

(1) Alteration of the function of Na+ channels may be of therapeutic utility for the treatment of muscle spasms, torticollis, tremor, learning disorders, and Alzheimer's disease. Polyamines which block slow sodium channels would have additional utility as local anesthetic agents. Agents which act on the epithelian Na channel would be useful adjuncts in the treatment of cystic fibrosis and asthma and as antihypertensive agents.

(2) Drugs which modulate the activity of K+ channels would be useful as protective agents against the damaging effects of anoxic and ischemic disorders and hypertension, and would act to protect red blood cells against damage in malaria and sickle-cell disease.

Calcium blockers (as well as other types of calcium modulators), used separately, are expected to yield information about how the event of cell death is organized.

Chideckel, E. W., et al., *Br. J. Pharmacol.*, 1986, 89:27-33 report that transient exposure to "polyamines" causes a relaxation of guinea-pig respiratory tract smooth muscle (trachealis muscle) in response to subsequent exposure to potassium ion extracellularly. This is contrary to the normal contractile response of this muscle exhibited in the absence of "polyamines" (or other calcium-ion entry blocking drugs such as nifedipine, verapamil, diltiazem or calcium ion-free solutions). The authors hypothesize *inter alia* that spermidine may have a $Ca^{3+}$ antagonist function and that spermidine and certain other polyamines may have a calcium channel blocking activity, "perhaps" similar to that of the known $Ca^{2+}$-entry blocking drugs referred to above.

Spermidine was the only polyamine tried in the experiments described in this article, although effects of other polyamines related to membrane $Ca^{2+}$ fluxes and cellular $Ca^{2+}$ handling are cited from other literature as follows:

putrescine is said to cause an increase in cytosolic $Ca^{2+}$ concentration in heart and kidney slices attributed to both an increase in extracellular $Ca^{2+}$ influx and a simultaneous release of $Ca^{2+}$ from mitochondria;

spermine is said to inhibit spontaneous contraction of the uterus muscle in a manner than can be counteracted by increasing extracellular $Ca^{2+}$ concentration;

spermine and spermidine are said to have a relaxant effect on smooth muscles of the gut, uterus, respiratory tact and vasculature.

The authors do not mention the type of calcium channels that are said to be present in trachealis muscle (or for that matter in the other tissues mentioned). As to trachealis muscle, dihydropyridine sensitivity indicates that L-type channels might be implicated. As to the other tissues mentioned, no claim is made in this article that calcium channels were involved (many other factors or processes could influence the concentration of calcium in the cytosol). In fact, some of the results reported in this article are inconsistent with blockage of calcium channels, and (based on the disclosure of this article) cannot be attributed to activation of calcium channels because of the many other factors that may be at work, including actions on potassium channels or direct action on smooth muscle (papaverine-like effects).

Hirsh, S. R., et al, *Psychopharmacology*, 1987, 83:101-104 report that two polyamines, spermine and spermidine, administered intraperitoneally, at doses of 5-40 mg/kg, in rats caused a dose-dependent inhibition of spontaneous climbing and wheel running behavior, which the authors tentatively attributed to modulation by these polyamines of limbic dopamine function. Hirsch et al. report further that the mice remained alert during the period of reduced locomotor activity and appeared to be in good health.

Injected intracerebrally (in the striatum), these compounds failed to induce asymmetric behavior. On the other hand, these compounds did antagonize hyperactivity (when injected into the *nucleus accumbens*) which the authors (erroneously according to the present inventors) considered consistent with modulation of dopamine function but not dopamine receptor blockage. No direct or indirect effect on ionic (or specifically calcium) conductance is disclosed or suggested.

The effects reported erroneously attributed to dopamine by Hirsh et al. are hereafter referred to as "spermidine-like" effects.

Palade, P., *J. Biol. Chem.*, 1987, 262:6149-6154 reports that the release of $Ca^{2+}$ (pre-loaded into isolated subfractions of sarcoplasmic reticulum) usually observed upon addition of various release-inducing substances (including caffeine and thymol) cold be blocked by ruthenium red, certain organic polyamines (spermine, spermidine and triethylene tetramine) certain antibiotics (neomycin, kanamycin, tobramycin, gentamicin, streptomycin and clindamycin) and certain polypeptides (polylysine, polyarginine, some histones and protamine). The authors observed that these agents have only one feature in common: the presence of several amino groups. Based on the inability of the polyamines to affect calcium pump function, the authors concluded that the effect of ruthenium red, spermine, neomycin and polylysine (which have quite diverse structures) was not due to interference with the $Ca^{2+}$ pump but to blockage of the sarcoplasmic reticulum calcium channels. Many of these agents appeared to block calcium release at (estimated) nanomolar concentrations. The authors also remarked that each compound's potency in inhibiting calcium release appeared to be related to the number of amine groups present in that compound: antibiotics appeared to be more potent on a molar concentration basis. However, since the experiments reported in this article measured only blockage of calcium release, they did not establish calcium channel involvement. Also, the reported results are limited to Ca²⁺ channels in the sarcoplasmic reticulum which have a large conductance (perhaps an order of magnitude greater than other known calcium channels) and, as stated by the authors, may be further limited to one type of Ca²⁺ channel in the sarcoplasmic reticulum. (The authors explicitly state that these compounds appear to be active on SR calcium channels that are insensitive to inositol triphosphate.). In general, SR calcium channels may be considered to be in a separate category not only because o their large conductance but also because of their location in the cell.

In a series of papers, Melchiorre, C., et al., report that certain polymethylene tetramines of the formula

(wherein Ar is an aromatic group; R, R' are hydrogen or methyl and m,n are various integer combinations within the range 5-14) have M-2 muscarinic receptor blocking activity in guinea-pig heart atria and intestinal ileum. Several of these compounds are said to selectively block the atrial muscarinic receptor with considerably higher affinity than the ileal receptor, and thus could possibly serve to distinguish between the two receptors. Nothing is disclosed about calcium channels, but a general synthetic scheme for the non-aromatic moieties of the disclosed polyamines is provided: *J. Med. Chem.*, 1989, 32:79–84; *J. Med. Chem.*, 1985, 28:1643–1647; and *Can. J. Physiol. Pharmacol.*, 1980, 58:1477–1483.

International Patent Application WO80/07098 discloses butyryl-tyrosinyl spermine and various analogs thereof which are said to be (potentially) useful for treating neurodisorders associated with an etiological agent binding to a glutamate receptor.

OBJECTS OF THE INVENTION

The present invention has the following objects:
to devise novel agents and methods for regulating (e.g. blocking, modulating or activating) ionic channels (including calcium, sodium, and potassium channels);
to devise novel agents and methods for regulating transmitter release or synaptic transmission;
to devise additional agents and methods for blocking ionic channels that overcome one or more of the disadvantages associated with known blocking agents described above;
to use each of such regulating agents and methods to design prototypical drugs that regulate calcium, sodium, and/or potassium channels (with emphasis on drugs that block channels of central neurons); and to increase the understanding of ionic channel structure, properties and function;
to design more active, less costly and/or otherwise improved substitutes for such agents and/or drugs;
to design agents that have calcium, sodium, and/or potassium channel modulating functions other than activation or blockage. For example, agents which act on the G-protein in cell membranes alter the activity of ionic channels indirectly and so do agents that act on the NMDA receptor.

Other objects of this invention will be apparent to those skilled in the art in light of the present specification, claims and drawings.

BRIEF DESCRIPTION OF THE DRAWINGS

FIG. 1A is a tracing of spontaneous firing activity observed in the guinea-pig Purkinje cell pursuant to application of a direct square current pulse (0.3 nA, 62 msec) in the absence of any blocking agents (control).

FIG. 1B is a tracing of the response of the Purkinje cell to a 0.45 nA direct square current pulse after addition of a mixture of compounds B and R: the calcium conductance is blocked.

FIG. 1C upper race is a tracing of the response of a Purkinje cell to a 0.45 nA direct square current pulse after (i) the P-channel has been blocked with a mixture of compounds B and R, (ii) the potassium conductance has been blocked with TEA, (iii) the sodium conductance has en blocked with TTX. The remaining spike is due to a calcium channel of the dihydropyridine-sensitive type. This is demonstrated in FIG. 1C lower trace where the L-channel also is blocked by dihydropyridine or FIG. 1D (lower trace) where the L-channel is blocked by streptomycin. (The upper trace in 1D is of the same type as in 1C.)

FIG. 9A traces the potassium channel activity in purified axon membrane to which a 50 mV/1 msec voltage is applied, prior to the addition of any compounds according to the present invention. The traces illustrate normal activity comprised of a number of potassium channels.

FIG. 9B is a single trace in two segments of the potassium channel activity in purified axon membrane to which 50 mV/1 msec voltage is applied one minute after the addition of compound (ZZ) at mM (high) concentration.

FIGS. 9C and 9D are traces of the potassium channel activity in purified axon membrane to which 50 mV/1 msec and 75 mV/1 msec voltage, respectively, are applied three minutes after the addition of compound (ZZ) at mM (high concentration.

SUMMARY OF THE INVENTION

Figure 2:
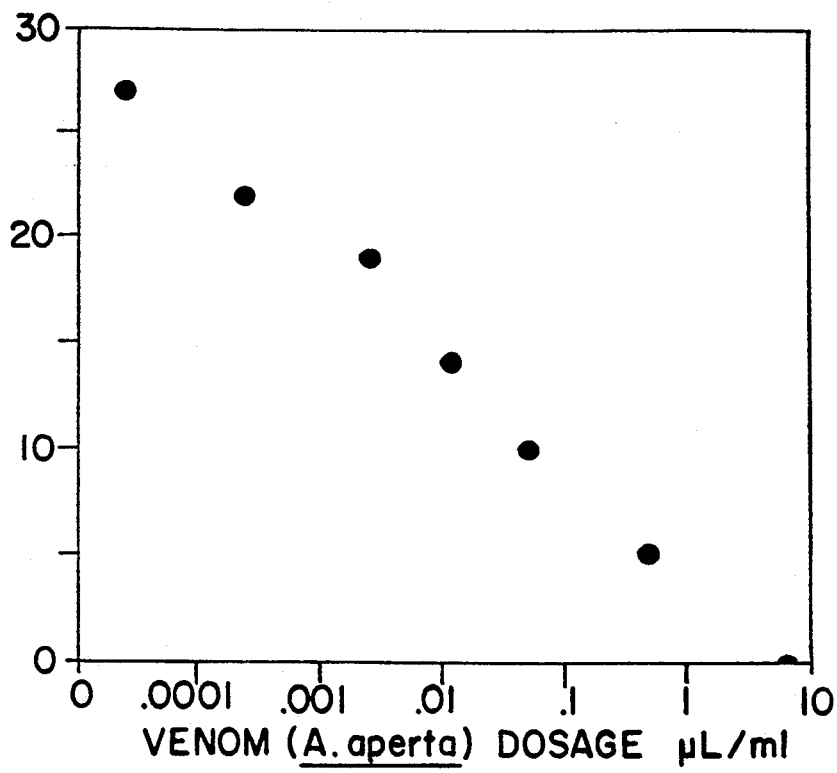
FIG. 2 is a graph of the presynaptic calcium current in the squid synapse observed after addition of various amounts of *A. aperta* venom in a voltage-clamp experiment demonstrating dose-dependence of this effect.

One aspect of this invention is directed to a method for regulating cation transport across cellular membranes possessing cation channels comprising exposing a cell membrane possessing an ion channel of a specific type, to a nonaromatic polyamine compound having a lysine- or arginine-based moiety (or a guanidine moiety) coupled to a straight chain polyamine.

Another aspect of this invention is directed to a method for regulating NMDA through a spermidine-like effect on NMDA receptors comprising exposing a cell membrane to compounds selected among the foregoing polyamine compounds.

In addition, the present invention is directed to the foregoing polyamine compounds themselves.

Other aspects of this invention are directed to methods for blocking calcium channels and to methods for blocking synaptic transmitter release using one or more of the compounds referred to above.

Another aspect of this invention involves methods for regulating ionic channels, either voltage- or ligand-gated such as the glutamate-activated channel (NMDA), by selecting a compound according to the present invention that is a calcium-, sodium-, or potassium blocker or modulator, and exposing a cell to the presence of this compound to bring about the desired specific regulating result on the target channel.

DETAILED DESCRIPTION OF THE PREFERRED EMBODIMENTS

The disclosure of any and all cited documents including literature and patent application is incorporated by reference in its entirety.

It is understood that in the present specification "ionic channel regulating agents" shall mean compounds and compositions which regulate flow of a cation by acting directly on a channel or by acting indirectly on it (e.g., by acting on another substance or cellular structure which in turn influences the function of an ionic channel).

Further, "block" shall mean the interruption of ion transport, with direct or primary block being directly attributed to the effect of the blocking agent, while indirect (or secondary or dependent) block is a result of, or due to the action of, the direct block. For example, direct block of a calcium channel may effectively block a potassium channel where potassium transport is dependent upon calcium transport.

In accordance with the present invention, certain nonaromatic polyamines have the ability to block calcium channels including P-type calcium channels (i.e. channels that display one or more of the characteristics associated with the P-channels first identified in Purkinje cells and described above).

As used herein, "polyamine" will generally refer to a compound that has (a) a dehydroxylated (or decarboxylated) arginine or lysine moiety (or a guanidine moiety) appended to (b) a straight polyamine chain moiety having two or more nitrogens separated by methylene groups.

Illustrative of polyamines useful as ionic channel regulating agents are the following compounds:

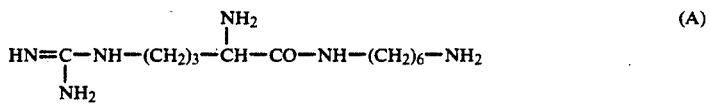

(A)

(weak potassium channel blocker - no activity on P-channel)

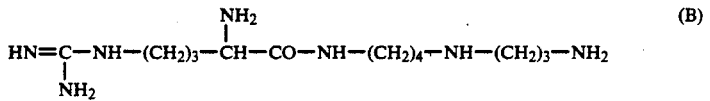

(B)

($Ca^{2+}$-channel blocker)

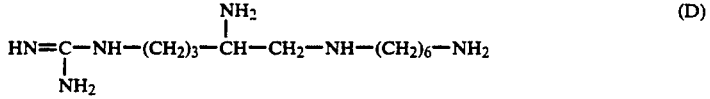

(D)

(potassium-channel blocker)

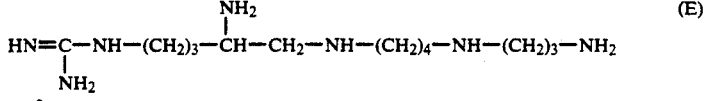

(E)

($Ca^{2+}$-channel blocker)

-continued

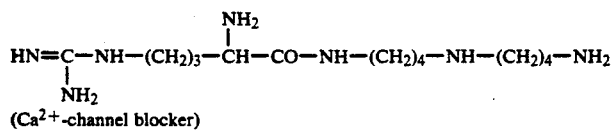
(sodium-channel blocker)

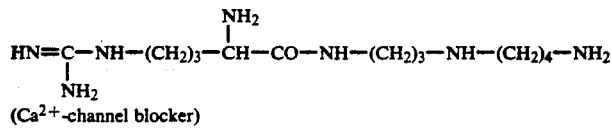
($Ca^{2+}$-channel blocker)

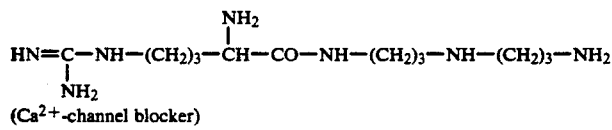
($Ca^{2+}$-channel blocker)

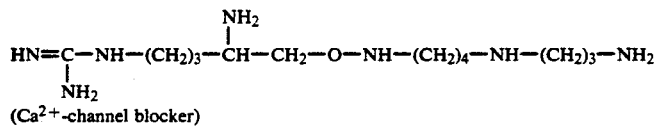
($Ca^{2+}$-channel blocker)

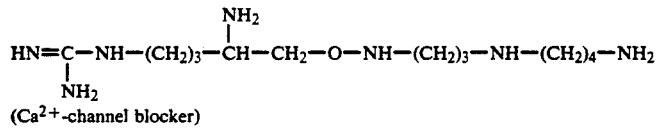
($Ca^{2+}$-channel blocker)

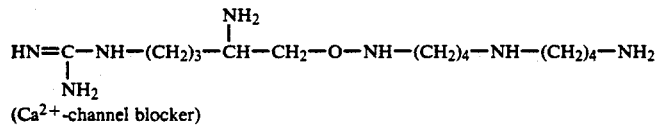
($Ca^{2+}$-channel blocker)

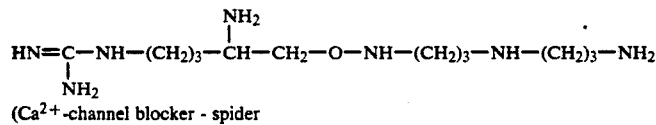
($Ca^{2+}$-channel blocker)

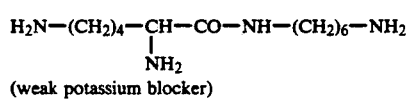
($Ca^{2+}$-channel blocker - spider venom factor (FTX)-like)

Examples of compounds having different channel blocking activity or displaying the same type of effect as spermidine when tested i.p. in animals (but with substantially greater potency) include derivatives or analogs of the above-listed compounds having, e.g., a dehydroxylated or decarboxylated lysine moiety.

Illustrative of polyamines useful as such regulating agents are the following compounds:

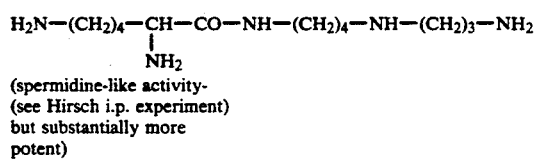
(weak potassium blocker)

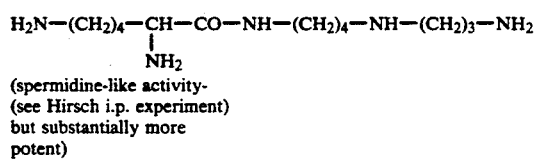
(spermidine-like activity-
(see Hirsch i.p. experiment)
but substantially more
potent)

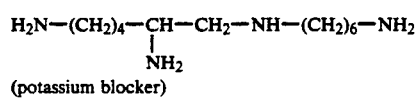
(potassium blocker)

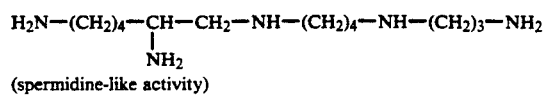
(spermidine-like activity)

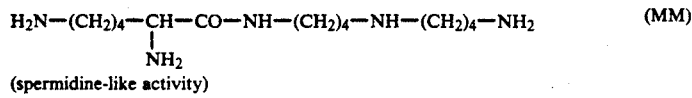
(MM)
(spermidine-like activity)

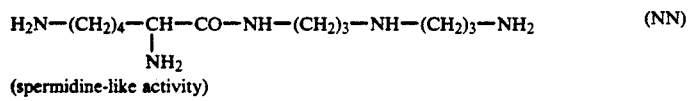
(NN)
(spermidine-like activity)

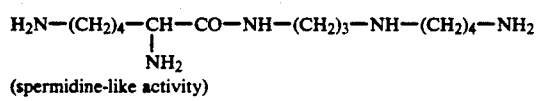
(spermidine-like activity)

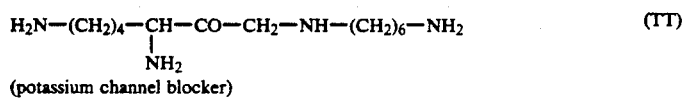
(TT)
(potassium channel blocker)

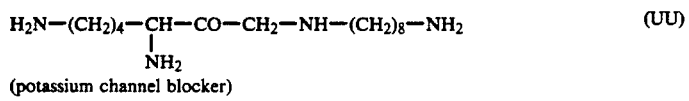
(UU)
(potassium channel blocker)

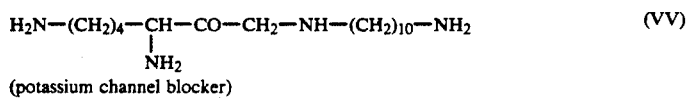
(VV)
(potassium channel blocker)

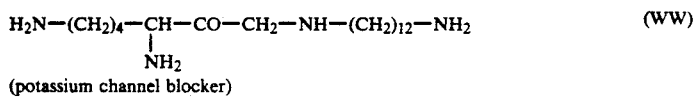
(WW)
(potassium channel blocker)

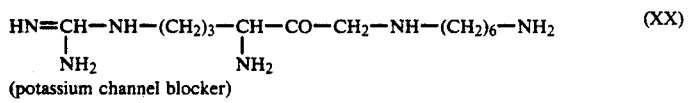
(XX)
(potassium channel blocker)

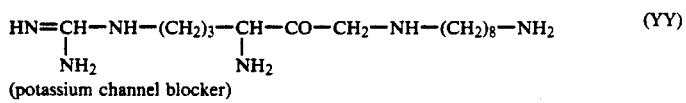
(YY)
(potassium channel blocker)

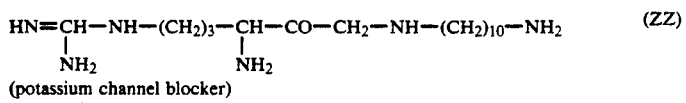
(ZZ)
(potassium channel blocker)

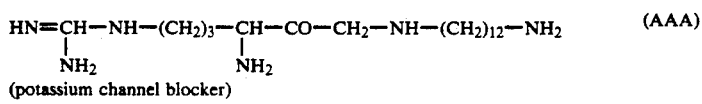
(AAA)
(potassium channel blocker)

In general, compounds of the formula
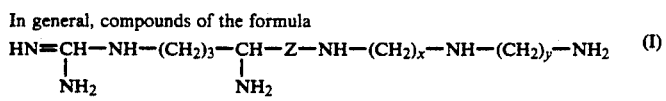
(I)

wherein x and y are integers independently selected from 3 or 4 and wherein Z is a carbonyl, $CH_2$, or single bond are calcium channel blockers similar to but more potent than spermidine. For example, compound S (which is the most preferred $Ca^{2+}$-blocking compound) was tested as per Example 1B and was fond to block calcium current in squid. In addition, compound S blocked $^{45}Ca^{2+}$-uptake in synaptosomes and Ca-dependent transmitter release at the neuromuscular junction synapses. The calcium blocking activity of compound S has been confirmed by single-channel studies. Compounds B and R also demonstrated such calcium-blocking activity e.g., in Purkinje cells and cerebellar granulocytes, however to different degrees.

In addition, in single-channel studies (eye epithelia), compound R was found to cause inhibition of chloride current, but this is believed to have been secondary to interference with calcium current (i.e. blockage of the so-called calcium-dependent chloride current was observed).

Compounds of the formula

wherein n is an integer between 6 and 12 inclusive, R is $H_2N-(CH_2)_4-CH(NH_2)$, or $HN=C(NH_2)-NH-(CH_2)_3-CH(NH_2)$ and Z is selected form the group consisting of CO, $CH_2$, or a single bond, are potassium current blockers in a manner independent of calcium ion flow. This was confirmed using each of several compounds within this formula in a purified axon membrane system. The compound wherein Z=CH₂ and n=10 is most preferred.

Compounds of the formula

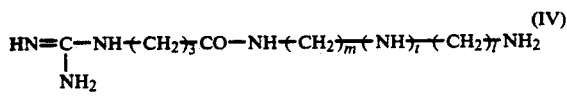

wherein t is zero or 1;
l is 3 or 4; and
m is 3 or 4 when t is 1 and m is zero when t is zero;
were demonstrated to be sodium channel blockers.

Finally, both the calcium blocking compounds and their analogs having a lysine moiety (even though the lysine-based analogs do not block calcium current) have effects observable at a gross level similar to those observed by Hirsch et al., supra, for spermidine but display substantially higher potency than spermidine (e.g. twice as potent). These effects may be related to activity of these compounds on the glutamate (NMDA) receptor, which in turn controls various ion channels.

The most preferred lysine-based compounds of Formula II are compounds wherein Z=CO, t=1 and m,l=3 or 4 (independently).

The polyamine compounds of the present invention can be synthesized using well-known and commercially available starting materials and synthetic schemes well-known in the art. Alternatively, polyamine compounds within the scope of the present invention may be obtained from commercial sources.

For example, decarboxylated arginine (agmatine), or arginine ethyl ester, decarboxylated lysine or lysine methyl or ethyl ester can be purchased from Sigma Chemical Co., St. Louis, Mo. Other well known polyamines such as spermine, spermidine, 1,6 diaminohexane and other diaminoalkanes, can also be obtained from Sigma or other commercial sources. Those polyamines which are not themselves active (e.g., spermine) can be used to synthesize active compounds as follows:

One protocol involves using an amine ester in aqueous solution and reacting it under basic conditions with an appropriate (usually equimolar) amount of a diamine or other polyamine also in aqueous solution (or in liquid form).

See, generally, March, J., *Advanced Organic Chemistry*, 3d. Ed., 1985, Wiley & Son, New York.

Other synthesis schemes for compounds within the scope of the present invention are disclosed in Eldefrawi, A. T., et al., *PNAS*, 1988, 85:4910-4913; Hashimoto, Y., et al., *Tetrahedron Letters*, 1987, 28:3511-3514; and Yamamoto, H., et al., *J. Am. Chem. Soc.*, 1981, 103:6133-6135 all of which can be employed with only such modifications, if any, as are readily apparent to those of ordinary skill in the art. Additional synthetic schemes may be readily devised based on International Application WO89/07098 published Aug. 10, 1989.

Another useful synthetic scheme which can be applied to the present compounds is the one disclosed in Melchiorre, et al., 1989, supra which involves use of a dicarboxylic acid to increase the length of a polyamine (in the presence of CH₃CH₂OCOCl, triethylamine and dioxane with addition of HCl and ethanol, followed by reduction in the presence of boron hydride, dimethyl sulfide and diglyme).

One preferred synthetic scheme for compounds within the scope of this invention that contain a decarboxylated arginine moiety (for example H₂N—(CH₂-)₃—CH(NH₂)—CH₂—NH—(CH₂)₃—NH—(CH₂)₄-NH₂ or H₂N—(CH₂)₃—CH(NH₂)—CH₂—NH—(CH₂-)₄—NH —(CH₂)₃—NH₂) involves reducing the appropriate protected amine ester, e.g., Z—NH—(CH₂-)₄—CH(NH—Z)—CO—OEt, (wherein Z is an appropriate protective group such as Ph—CH₂—O—CO— wherein Ph is phenyl) in the presence of THF (at —78 degrees C.) and di-isobutylaluminum hydride to the corresponding aldehyde, aminating this product in the presence of sodium cyanoborohydride to produce the desired polyamine which can then be deprotected and purified according to well-known methods.

Alternatively, the protected amino acid (e.g. the free acid corresponding to the ethyl ester referred to above) can be first converted to the corresponding mixed anhydride by reacting with, e.g., Et—O—CO—Cl (ethoxycarbonyl chloride) and TEA (triethylamine) and THF (tetrahydrofuran) at —20 degrees C. The anhydride can then be reacted with an alcohol, e.g., methanol at —10 degrees C. in the presence of sodium borohydride to convert the mixed anhydride to the corresponding alcohol. The alcohol can then be converted to the corresponding halide according to well-known halogenation techniques. The halide can be condensed with the appropriate amine (in the presence of an acid scavenger such as K₂CO₃ or dimethyl formamide) to yield the target protected compound which can be deprotected by e.g., hydrogenolysis (H₂ palladium/carbon 10%) or where the protecting group is Boc, with trifluoroacetic acid to yield the actual target compound.

Compounds within the formula I wherein R does not have an alpha amino group appended to a —CH group and their isomers (e.g., HN═C(NH₂)—NH—(CH₂-)₄—NH—(CH₂)₄—NH—(CH₂)₃—NH₂) can be synthesized from the appropriate polyamine (for example, H₂N—(CH₂)₄—NH—(CH₂)₄—NH—(CH₂)₃—NH₂) using a guanylating agent such as 3,5-dimethyl-1-guanyl pyrazole nitrate under ethanol reflux. The target compound can be isolated as the nitrate. (Guanylating reaction.)

When used as laboratory reagents the compounds of the present invention can be used in widely ranging units from nanomolar to no particular upper limit. It will be appreciated that the amount that needs to be used in each instance will depend on the activity of a particular compound (whether the compound is a potent blocker, or modulator), on the sensitivity of the specific channel on which this compound is active (whether the channel properties are easily modifiable), on the specificity of the activity of the particular compound (whether the compound acts exclusively on one type of channel) and on other factors which are well-recognized in the art to be subject to optimization. Such optimization can be easily achieved without undue experimentation by well-known methods.

When the compounds of the present invention, including pharmaceutically acceptable salts thereof are used for pharmaceutical purposes (for example to bring about the behavioral modifications or to treat the behavioral disorders referred to herein), they may be incorporated in pharmaceutical compositions in oral, enteral, topical, depot, or parenteral dosage forms containing one or more of the present compounds, in association with one or more pharmaceutically acceptable excipients, fillers, salts, coatings, carriers or diluents such as are customarily used with pharmaceutical preparations, e.g., tablets, sustained-release preparations, gelatin capsules, injectable solutions, suppositories, or coupled to a drug delivery system, etc. The active ingredient dosage ranges will encompass the following preferred ranges: 10-100 mg/kg of a particular compound or compounds in rodents, and 0.05-50 mg/kg in man. It will of course be preferred to use the minimum amount which will accomplish the desired effect in order to avoid as many potential side effects as possible. Moreover, the unit content of each dosage form need not by itself constitute an effective amount of active ingredient since a plurality of dosage forms may be administered to achieve an effective amount in combination. In addition, the amount used and the duration of the treatment will also be subject to optimization and will vary depending on the severity and responsiveness of the condition to be treated, the age, weight, and physical condition of the patient, and often also on the administration route.

The invention is further described below by reference to specific Examples which are intended to illustrate it without limiting its scope:

EXAMPLE 1 ASSAYS FOR P-CHANNEL BLOCKING ACTIVITY

A. Purkinje Cell System

Adult Hartley guinea pigs (400-600 grams from Camm Research Institute, Wayne, N.J.) were decapitated with a small animal guillotine under ether or sodium pentobarbital (Abbott Pharmaceuticals, Inc., N. Chicago, Ill., 40 mg/kg i.p.) anesthesia. A rapid craniotomy was performed to remove the squamous portion of the occipital bone, which allowed the total cerebellar mass, including the cerebellar nuclei, to be detached quickly with a metal spatula. The tissue was then immediately immersed in aerated Krebs-Ringer solution containing 124 mM NaCl; 55 mM KCl; 1.2 mM $KH_2PO_4$; 2.4 mM $NaCl_2$; 1.3 mM $MgSO_4$; $NaHCO_3$ (26 mM); and 10 mM glucose. This solution was kept refrigerated at 6° C. The cerebellar mass was then transacted sagitally and a single cell slice about 2 mm thick was isolated from the vermis or from one of the hemispheres. The slice was affixed with cyanoacrylate to the bottom of a plexiglass cutting chamber and agar blocks were used to surround the slice, thus providing side support. Once secured, the tissue was immersed in Krebs-Ringer solution at 6° C. and further sectioned with an Oxford G501 Vibratome (Ted Pella, Inc., Tustin, Calif.) to yield about six 200- or 300-micron thick cerebellar slices, containing sagittal sections of all the cerebellar folia in a given rostrocaudal plane as well as central white matter and cerebellar nuclear cells. Following this procedure, the slices were incubated in oxygenated (95% $O_2$; 5% $CO_2$) Krebs-Ringer solution at 37° C. for about one hour.

After incubation, a slice was transferred to a recording dish such as that described in Llinas, R. et al, *J. Physiol.*, 305:171, 1980. The cerebellar slice was placed in a Sylgard plate (Corning Glass, Corning, N.Y.) at the bottom of the recording chamber and secured with a bipolar stimulating electrode pressing lightly on the white matter. The experiments were conducted at a chamber temperature of 37° C. maintained by a surrounding temperature-controlled water bath. The saline (Ringer's) solution used for continuous perfusion was also kept at 37° C.

Various channel blocking agents were used to block conductances under study or to block ionic conductances that would interfere with a particular experiment: Tetrodotoxin ("TTX" $10^{-6}M$) was used to block sodium conductance, triethylammonium chloride ("TEA", 30 mM), was used to block potassium conductance; nitrendipine ($10^{-5}$-$10^{-6}M$) was used to block the L-channel.

Various preparations of compounds to be tested for P-channel blocking activity were introduced in the bath and the flow was turned off for various time periods. These preparations were added in aliquots of 20-40 microliters from a solution containing a particular molar concentration of each substance to be tested. The volume of the extracellular bath was 4 cc.

Purkinje cells were impaled with recording micropipettes under direct vision using Hoffman modulation microscopy (Hoffman, R., *J. Microsc.* 110:205-222, 1977). Intracellular recordings were obtained wthi micropipettes filled with 3M potassium acetate or 1M tetraethylammonium chloride (TEA), and having an average D.C. resistance of 60-80 mega ohms. Synaptic activation of the cells was effected with a bipolar stimulation electrode located on the white matter at the basis of the folium studied. Direct simulation of the Purkinje cells was implemented with a high-input impedance ($10^{12}$ Ohms) bridge amplifier.

In this series of experiments, various concentrations of the compound being tested were used as specified below: The smaller the amount of active compound that achieves blockage the higher the affinity of the active polyamines for calcium channels. Representative results of the experiments described below are illustrated in FIG. 1.

Before the introduction of a polyamine or other channel blocking compounds in the bath, upon injection of an outward (depolarizing) current pulse, the neurons responded with firing having both sodium-dependent and calcium-dependent spikes in accordance with the normal electrical response of the Purkinje cells in the absence of a P-channel blocker (FIG. 1A). The cell responses were also measured at several time intervals after introduction of a polyamine compound in the recording chamber medium. Typically, in the presence of a P-channel blocker, a small depolarizing current (approximately 0.3 o 0.45 nA for 62 msec) generates a burst of potential spikes and a plateau potential, the latter due to the non-inactivating ("persistent") sodium conductance; calcium spikes are substantially reduced or extinguished and there is no calcium-dependent component to the plateau potential (FIG. 1B). FIG. 1B was recorded after the addition of a mixture of compounds B and R to a final concentration of 0.8 mM.

The apparent absence of the sodium-dependent fast spikes in FIG. 1B that would be expected to follow the first such spikes observed is due to the substantially increased resistance of the cell (indicated by the sodium-dependent plateau potential). Blockage of calcium channels precludes calcium ions from entering the cell and consequently the exit from the cell of potassium ions is not activated. The results in FIG. 1B are comparable to addition of the P-channel blocker isolated form funnel-web spider venom, e.g., *A. aperta*, as disclosed in U.S. patent application Ser. No. 219,905.

In FIG. 1C (upper trace), potassium conductance was blocked with TEA which was also added to the bath (which already contained TTX and a mixture of compounds B and R. The remaining calcium spike is due to the existence of another type of calcium channel in Purkinje cells. (The P-channel has been blocked by a mixture of compounds B and R as in the experiment of FIG. 1B). The spike of FIG. 1C is due to a calcium conductance that is polyamine-resistance (and funnel-web venom resistant) and is therefore not due to the P-channel. This remaining calcium conductance is blocked by the addition of dihydropyridine (FIG. 1C, lower trace) and is also blocked by the addition (to the same preparation, 1D upper trace) of antibiotics such as streptomycin (FIG. 1D, lower trace).

B. Electrophysiology with Squid Stellate Ganglia

Figure 4:
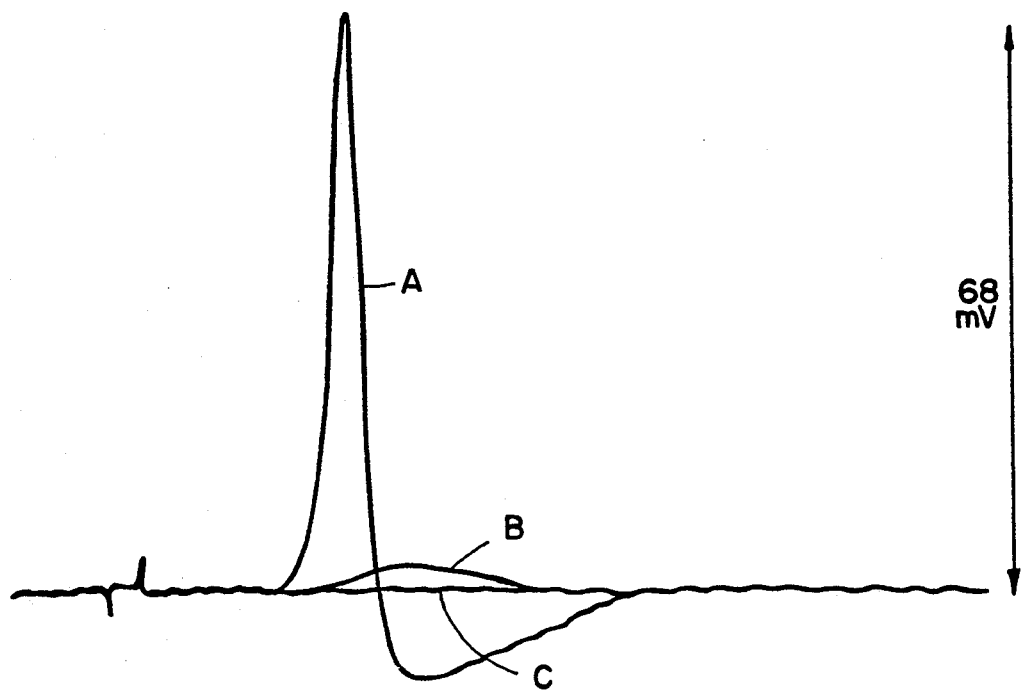
FIG. 4 shows the postsynaptic action potential in squid synapse pursuant to direct stimulation of the presynaptic terminal. Tracing A was recorded prior to the addition of a mixture of compounds B and in the bath (0.15 ml of the preparation of Example 2); tracing B was recorded 4 minutes after the addition of a mixture of compounds B and R; and tracing C was recorded 6 minutes after addition of a mixture of compounds B and R.

In squid synapse voltage clamp and current clamp experiments, the following observations were made:

Action potentials were induced by direct electrical stimulation of the presynaptic nerve bundle of the giant synapse in squid stellate ganglia. The thus evoked postsynaptic action potential is shown in FIG. 4 in the absence of any calcium-blocking agents in the bath (trace A). After addition in the 3 cc bath of 0.15 ml of the preparation of a mixture of compounds B and R (described below), the postsynaptic action potential is markedly reduced (trace B) four minutes after such addition and completely extinguished at 6 minutes.

The decrease and eventual extinction of the postsynaptic action potential is attributed to blockage by the P-channel blocking factor (here a mixture of compounds B and R) of the presynaptic calcium channels.

Figure 6:
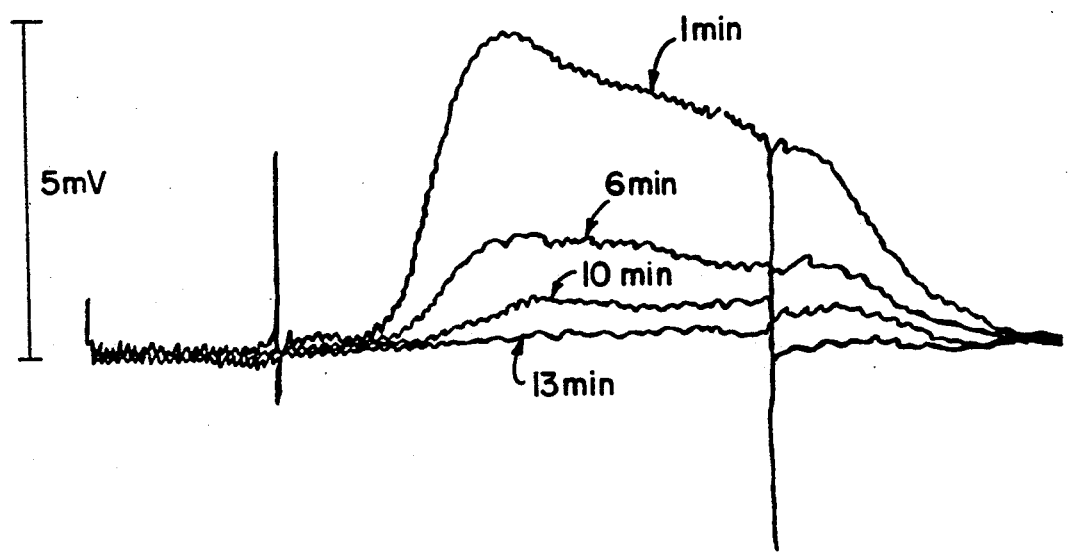
FIG. 6 is the trace of the postsynaptic potential again in squid synapse after application of a 38.2 mv/10 msec voltage step in a voltage clamp experiment in the presence of TTX and 3-aminopyridine. Recordings were made 2, 6, 10 and 13 minutes after the addition of a mixture of compounds B and R.

That calcium channels are involved was demonstrated in another type of voltage clamp experiment (FIG. 6) in which the postsynaptic potential in squid synapse (in a preparation containing tetrodotoxin and 3-aminopyridine) is reduced over time after the addition of 0.4 ml of a 1 mM solution of the P-channel blocker mixture of compounds B and in the 3 cc bath. In FIG. 6, the squid postsynaptic action potential evoked by a 38.2 mV voltage clamp for 10 msec from a resting potential of $-60$ mV was recorded, 1, 6, 10 and 13 minutes after addition of the P-channel blocker. The potential was reduced and eventually extinguished. It should be noted that squid synapse is less accessible to reagents than Purkinje cells; therefore greater amounts of a blocking agent and/or a longer waiting time are necessary for a particular effect to be observed.

Figure 5:
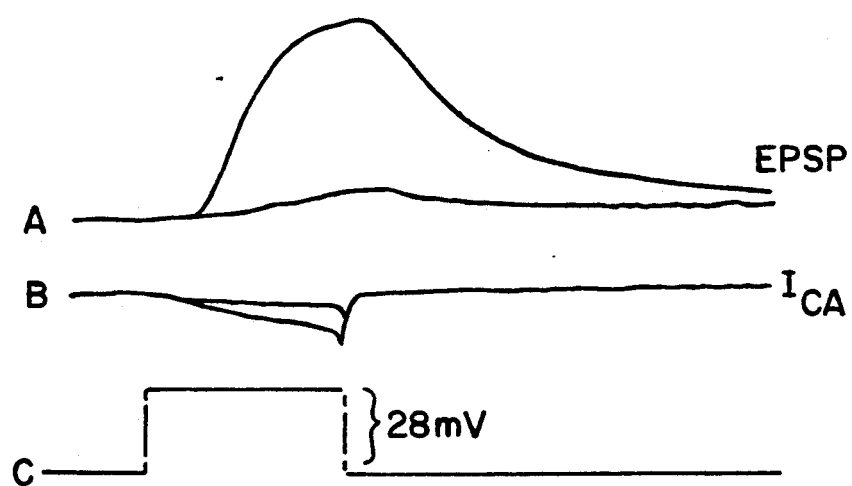
FIG. 5 upper trace is the postsynaptic potential (EPSP) response in squid synapse in a voltage clamp experiment before (A) and after application of a mixture of compounds B and R in the bath (which already contained TTX and 3-aminopyridine). The middle trace is the presynaptic calcium current before (A) and after application of a mixture of compounds B and R in the bath. The lower trace is the applied voltage step (28 mV, 5.5 msec).

FIG. 5 shows yet another voltage clamp experiment in which a 28 mV/5.5 msec voltage step is applied to the presynaptic terminal (trace C) in a squid synapse preparation, wherein sodium conductance was blocked with TTX and potassium conductance was blocked with 3-aminopyridine. The applied step voltage generates a compensating inward ionic current in the presynaptic cell (trace B) which is due solely to calcium since the other conductances are blocked. At the postsynaptic cell a postsynaptic potential (EPSP) is evoked, which is the normal response (upper curve, trace A) in the absence of a P-channel blocker (here a mixture of compounds B and R). At the same time, in the presence of the mixture of compounds B and R, the presynaptic ionic current is also reduced (trace B, upper curve, i.e. curve with the lesser amplitude).

This indicates that the P-channel blocker acts on the presynaptic calcium channels since the time relationship in FIG. 5 of the presynaptic calcium entry to the postsynaptic response remains constant and only the amplitude of the postsynaptic response is reduced in direct relationship to the reduction of the presynaptic calcium current. This means that the P-channel blocker blocks presynaptic calcium channels which impedes calcium influx and consequently the expected transmitter release does not occur. The reduced transmitter release in turn causes a reduced postsynaptic response.

Figure 7A:
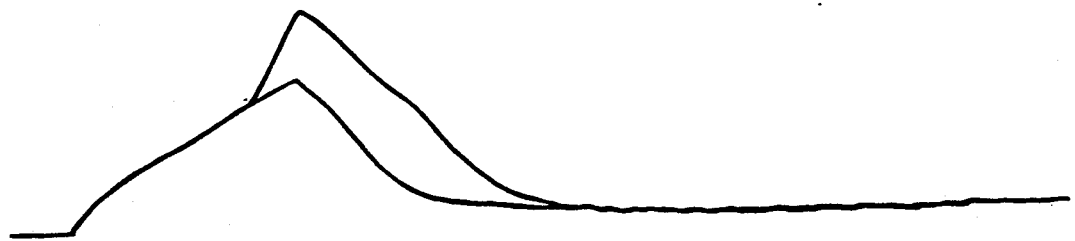
FIG. 7A and B are traces of the presynaptic and postsynaptic potential in squid synapse in the absence (upper trace) or presence (lower trace) of calcium blocker.

In a current clamp experiment using squid synapse, a fixed amplitude depolarizing current (400 nA, 8.4 msec) is applied to the presynaptic terminal. In the presence of TTX and 3-aminopyridine, the presynaptic potential (calcium spike) is as depicted in FIG. 7A, upper trace.

Figure 7B:
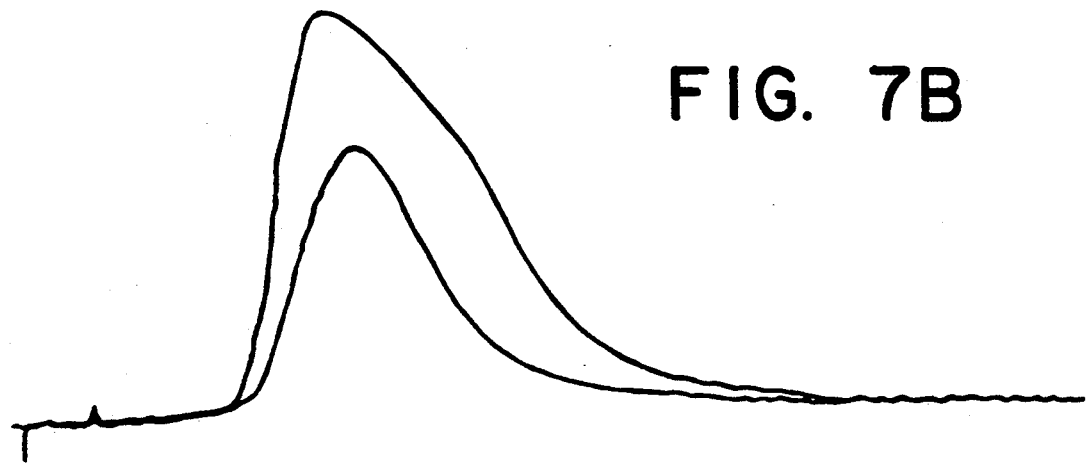

The corresponding postsynaptic potential (EPSP) is depicted in FIG. 7B (upper trace). Seven minutes after addition of P-channel blocker (here a mixture of compounds and R) the presynaptic calcium spike is reduced (77A, lower trace) and so is the EPSP (7B, lower trace). The presynaptic calcium spike after blockage varies in amplitude only. The evoked postsynaptic potential also varies in amplitude. Moreover, the time course of the EPSP after blockage is the same as in the absence of blocker. This indicates that the polyamine P-channel blocking agents act presynaptically and do not have a postsynaptic effect: if a postsynaptic blockade was present, the time course of the EPSP would also be different (in addition to its amplitude being lower).

Figure 3:
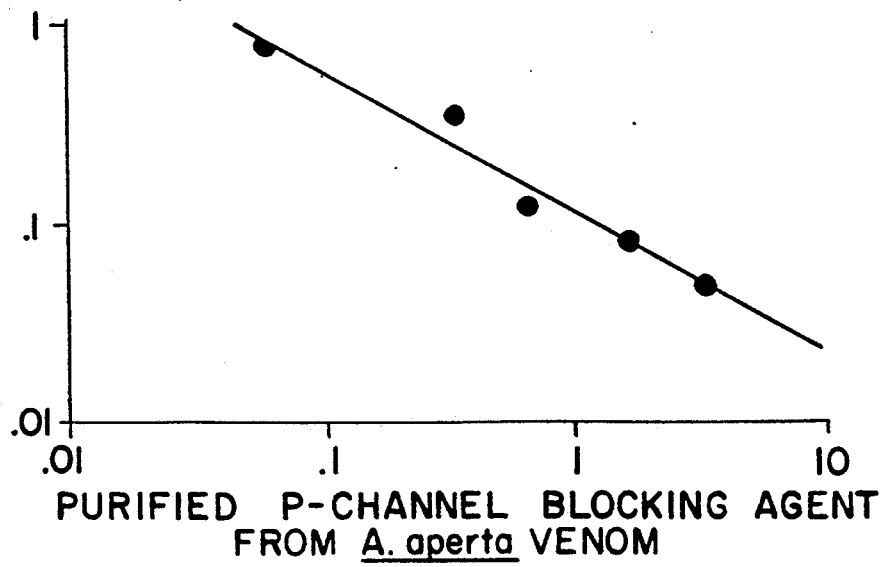
FIG. 3 is a graph showing the fraction of the excitatory postsynaptic potential (EPSP) remaining (with the control taken as 1) after addition of various amounts of partially purified P-channel blocking factor from *A. aperta* venom in squid synapse. The results demonstrate the dose-dependence of the effect by the factor on the EPSP.

FIGS. 2 and 3 demonstrate that the effect of the P-channel blocking agent on the presynaptic calcium current and postsynaptic potential is dose-dependent: both decrease in amplitude with an increasing amount of P-channel blocker used in the extracellular medium. (In FIG. 2 venom was used and i FIG. 3 partially purified *A. aperta* P-channel blocker was used). he partially purified preparation was processed by deproteination from venom (boiling), centrifugation, removal of the pellet, addition to original volume of water followed by twice butanol extraction in 20 volumes of butanol. The aqueous phase was used.

The results described herein are qualitatively the same regardless of the particular P-channel polyamine blocker used. The only difference is the potency of the particular blocker. The mixtures of compounds B and R appeared to be much more potent than spermidine, and, for that reason, these compounds are prepared.

EXAMPLE 2 POLYAMINES USED FOR REGULATION OF CHANNELS

The following compounds were purchased or synthesized and tested for ion channel blocking activity.

The following were obtained form Sigma:

| | |
|---|---|
| spermidine | $NH_2-(CH_2)_4-NH-(CH_2)_3-NH_2$ |
| 1,6 diaminohexane | $NH_2-(CH_2)_6-NH_2$ |
| spermine | $NH_2-(CH_2)_3-NH-(CH_2)_4-NH-(CH_2)_3-NH_2$ |

In addition, L-arginine ethyl ester

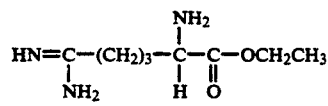

also from Sigma was used to synthesize compounds B and A, above. Briefly, the synthesis of Compound B involved use of $3 \times 10^{-3}$ moles of L-arginine ethyl ester which was dissolved in 5 ml of 1N NaOH. An equimolar amount of spermidine was added dropwise and the reaction was allowed to proceed at 25° C., pH 14 under stirring. The product was brought to pH 7.4 by addition of 5N HCl. Forty-microliter aliquots of this preparation of Compound B were used in experiments with the assay system of Example 1.

Compound A was synthesized in the same manner except that an equimolar amount of $NH_2$—$(CH_2)_6$—$NH_2$ was first dissolved in a minimum volume of water before adding to the arginine ester in 1N NaOH.

Compound E (4,3) and its isomer (3,4) can be synthesized by a quanylating reaction, as described above.

In addition, several antibiotics containing polyamine moieties were obtained commercially and tested. These were:

Gentamycin (from Elkins-Sin, Inc., Cherry Hill, N.J.).

Streptomycin (Pfipharmecs, a division of Pfizer, Inc., New York, N.Y.).

Vancomycin (Eli Lilly Industries, Inc., Carolina, Puerto Rico).

It is anticipated that other antibiotics containing amine groups such as Kanamycin will have the same activities, any differences being of degree rather than kind. Several such antibiotics are commercially available.

Each of the three antibiotics listed above as having been tested was dissolved in water and 0.1, 0.4, and 0.8 mM amounts were used. 1 mM of vancomycin was used.

Finally, the compounds 4-(3-aminopropyl) morpholine from Aldrich Chemicals Milwaukee, Wisc., and PHTX433 ("PTX433"), a compound described in Eldefrawi et al., 1988, supra (believed to be a glutamate receptor antagonist for locust leg muscle) were also tested.

Amounts of up to 1.0 mM of the morpholine derivative and even larger amounts of PTX433 were used for electrophysiological evaluation of their P-channel blocking activity.

The compounds

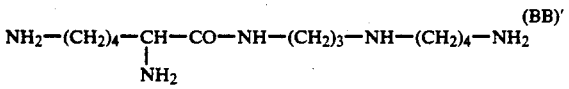

(BB)' and

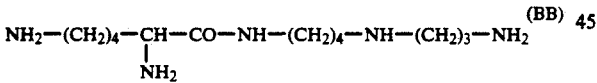

(BB)

were synthesized by reacting an equimolar mixture of lysine and spermidine in water, in the presence of an equimolar amount of a water-soluble carbodiimide namely N-cyclohexyl-N'-((2-morpholinyl)-ethyl)-carbodiimide-methyl-p-toluene sulfonate (Aldrich Chemical Co.) at pH 4.7. The reaction mixture was allowed to remain 20 hours at room temperature under stirring. The product mixture was extracted three times with ethyl acetate (total about 10 volumes) and the aqueous phase was recovered and brought up to pH 7.2. The aqueous phase can be further purified by FPLC (high performance liquid chromatography-Pharmacia) under a 0-1.0 NaCl gradient, pH 7.5 and a flow rate of 1 ml/min using a cation-exchange column such as Mono-S (5×50 mm) from Pharmacia. Alternatively, another conventional further purification method can be used. However, the aqueous phase resulting from the above-described final ethyl acetate extraction can be used as is.

Although the foregoing synthesis method does not differentiate between the two compounds (BB) and (BB)' and in all likelihood yields a mixture of these compounds, the activity of the extracted product indicates that both are active. (This mixture and other similar mixtures can be separated and the individual compounds purified by chromatographic techniques using e.g. silica gel or a DOWEX cation exchange column.)

The foregoing technique can be used to synthesize other lysine-based polyamines within the invention.

Another synthetic technique that can be used to yield only compound (BB)' is to first react the lysine with 1,3 diamino propane sing, e.g., the above carbodiimide method, and then reacting the product (preferably) after purification with 1,4 diamine butane using one of the methods described above for the arginine-polyamine compounds. The order of use of the diamines can be reversed for synthesizing the (BB) product. The technique can be applied to synthesis of other compounds of the invention.

EXAMPLE 3 FURTHER STUDIES

Compounds B and R are lethal to rates when administered at a dose of 50 to 100 microliters. Similar amounts of purified compound BB do not kill these animals. On observation, rats are placid but display no visible movement disorders, and do not extend their limbs when picked up. Compound BB (and/or BB') appeared to have a calming effect similar to a tranquilizing effect but without much muscle relaxation.

EXAMPLE 4 FLUORESCEIN-LABELLING OF CALCIUM-REGULATING AGENTS

Arginine was labelled by mixing with an equimolar amount of fluorescein in sodium borate buffer, pH 9.5 and allowing the mixture to react overnight in the dark under stirring. Excess fluorescein was extracted by washing these times with 10 volumes ethyl acetate per wash. The thus labelled arginine can be used to synthesize compounds of Formula I. Lysine ethyl ester can be similarly labelled. Thus, labelled Formula I compounds can be used in fluorescence experiments, using methods well-known in the art.

EXAMPLE 5 RESULTS OF FURTHER ELECTROPHYSIOLOGICAL STUDIES

P-channel activity was recorded in the system of Example 1 in the absence and presence of various amounts of the compounds listed in Example 2.

The results for the P-channel were as follows:

Spermine and 1,6 diaminohexane did not block the P-channel at the concentrations tested (up to about 1 mM). The calcium conductances attributable to P-channels were the same in the presence and in the absence of these compounds. By contrast, spermidine blocked the P-channel selectively but not with high potency (compared to the potency of spider venom or purified P-channel blockers from venom).

4-(3-aminopropyl)morpholine did not block the P-channel up to a concentration of 1 mM. PHTX433 did not block the P-channel up to a concentration of 10 mM in Purkinje cells, but blocked the postsynaptic response in squid (about 300 micromolar).

By contrast, the mixture of compounds B and R was a potent P-channel blocker producing complete P-channel blockage at concentrations lower than 0.5 mM. The other channels (sodium, potassium) were not affected. The minimum effective concentrations of the P-channel blocking agents of this invention are micromolar or less;

this can be determined by routine experimentation using serial dilutions of these agents. Preferred are concentrations up to 1 mM but it should be appreciated that the choice of concentration of each agent is subject to optimization as is well-known in the art and also depends on whether partial or total P-channel blockage is desired.

The antibiotics block the sodium channel at concentrations below 1 mM. None of the antibiotics tested block the P-channel at concentrations below 1 mM although P-channel blockage is seen (as well as L- and sodium channel blockage) when the concentration of the aliquot introduced in the bath is higher than 10 mM. In no instance was P-channel blockage by the antibiotics potent or specific, despite the presence of the arginine-like moiety HN=C(NH$_2$)—NH— in streptomycin and of various amine groups in the other antibiotics.

EXAMPLE 6

A mixture of compounds (BB) and (BB)' was administered to a rat in amounts ranging between 50 and 100 mg/kg. The rat was subsequently injected with 40 mg/kg (actual volume: 0.2 ml) of sodium phenobarbital (NEMBUTAL), a dose which normally produces total anesthesia, and in many cases death. The (BB)/(BB)'-injected rat by contrast, did not become unconscious upon injection. It took two additional doses of nembutal to anesthetize this rat. The experiment was repeated except this time two rats were injected with a mixture of compounds (BB) and (BB)', one with the same dose as was administered in the previous experiment and one with twice that dose. Immediately after injection, the first rat appeared normal and the second exhibited reduced activity on observation. After each was injected with 40 mg/kg of nembutal, the first rat showed no effect but the second appeared to wake up. Subsequent 40 mg/kg injections of Nembutal caused the first rat to become anesthetized at a total dose of 160 mg/kg but the second rat received a total of 200 mg/kg before he was anesthetized, and received 240 mg/kg before he was killed. The normal LD-50 for Nembutal in rats is about 60 mg/kg. Therefore this dose is enormous by comparison. The implication is that mixtures of compounds (BB) and (BB)' cause resistance to barbiturate action. Furthermore, the mixture causes animals to be serene without being tranquilized, in that it does not cause much muscle relaxation and has potential utility as a prototype drug anxiolysis.

EXAMPLE 7 $^{45}$Ca BLOCK OF SYNAPTOSOMES

A. Preparation of Synaptosomes

Cerebral cortex from three rats was homogenized in 0.32M sucrose using a manual driven Teflon glass homogenizer. The homogenate was centrifuged at 4° C., 3000 g for 10 minutes, and the supernatant was further centrifuged at 50,000 g for 20 minutes. The pellet was resuspended in sucrose 0.32M and seeded in a 0.8-1.4M sucrose gradient. After 2 hours of centrifugation at 25,000 g, the bands in 0.1-1; 1-1.2 and 1.2-1.4M layers were pooled and slowly diluted, 1:4 in NaCl 132 mM Ca$^{2+}$ free solution. After 35,000 g centrifugation for 15 minutes, the pellet was resuspended in (A) Choline Cl 132 mM, CaCl$_2$ 1.2 mM or in Choline Cl 65 mM CaCl$_2$ 1.2 mM solution. Samples from A and B suspension (500 ul, 1 mg/ml of protein) were incubated for 10 minutes at 32° C. with or without the tested toxin.

B. $^{45}$Ca$^{2+}$ Uptake

In nerve terminals, calcium influx into synaptosomes can be estimated by measuring the $^{45}$Ca$^{2+}$ uptake when synaptosomes are depolarized by K.

$^{45}$Ca$^{2+}$ uptake was started by the addition of 0.3 uC/uMol of $^{45}$Ca$^{2+}$ diluted in 200 ul Na ringer for basal uptake or Na K ringer for K stimulated uptake (final concentration 65 mM). The Ca$^{2+}$ uptake was stopped after 15 or 30 seconds with the addition of 3 ml of EGTA (ethylene glycol bis (amino-ethyl-ether) N, N, N', N'-tetra acetic acid) (4 mM) buffer solution. This suspension was rapidly filtered under vacuum through Whatmann GF/B filter paper and washed 3 times with the washing solution (Choline Cl 132 mM; KCl 5 mM, CaCl$_2$ 1.2 mM, MgCl$_2$ 1.3 mM, glucose 10 mM, Tris 5 mM pH 7.4). Filters were dryed and immersed in scintillation fluid and counted in a scintillation counter. Compound S was prepared by processes similar to those described in Nakanishi et al., International Patent Application No. WO89/07098, particularly pages 18-19 and Yamamoto et al., J. Am. Chem. Soc., 1981, 103:6133-6136, starting with NH$_2$—(CH$_2$)$_3$—NH$_2$. For comparison, FTX was purified chromatographically from the crude venom of American funnel-web spiders (Spider Pharm, Black Canyon, Ariz.

C. K Stimulated $^{45}$Ca$^{2+}$ Uptake by Synaptosomes

1. Compound S

Compound S was an effective inhibitor of the K induced $^{45}$Ca$^{2+}$ uptake in cerebral cortex synaptosomes. submillimolar concentrations of Compound S were capable of blocking the $^{45}$Ca$^{2+}$ uptake in a dose dependent manner.

2. Comparative Data

FTX (0.7 ul/ml) reduced $^{45}$Ca$^{2+}$ uptake to the same level as the non-depolarized synaptosomes. However, 100 uM Cd was more effective since it also blocked part of the non K dependent uptake.

As an additional control, the effect of spermidine was studied. A concentration up to 3 mM of spermidine lacked of any effect of neuromuscular transmission. Spermidine showed no significant blocking effect.

This demonstrates that cerebral cortex synaptosome Ca$^{2+}$ is sensitive to Compound S in a manner similar to FTX. However, Compound S can be readily synthesized and is identifiable, unlike FTX.

EXAMPLE 8 EFFECT ON Ca DEPENDENT TRANSMITTER RELEASE IN THE NEUROMUSCULAR JUNCTION

A. Muscle Preparation

Nerve-muscle preparations were obtained from male Swiss mice (25-30 g) by removal after cervical dislocation and pinning out in a Sylgard (R) coated chamber containing 1-2 ml of physiological solution consisting of (millimolar) NaCl, 135; KCl, 5; CaCl$_2$, 2; Mg$_2$SO$_4$, 1; NaHCO$_3$, 12; NaH$_2$PO$_4$, 1; d-glucose, 11; pH 7.4 kept at room temperature. The solution was oxygenated by continuous bubbling with a mixture of 5% CO$_2$ and 95% O$_2$. Intracellular recordings of miniature endplate potentials and evoked endplate potentials were performed. Glass microelectrodes filled wthi 2M KCl of 5 to 15 MOHM resistance were used. The electrodes were inserted into the muscle fibers near the endplate regions, which were located visually by the ends of intramuscular branches of the phrenic nerve. The mean quantal content (m) of transmitter release was measured in muscles incubated in low $Ca^{2+}$ (1.2 mM) high $Mg^{2+}$ (6 mM) based on the failure method, where m=log e N/Nf and N is the total number of nerve stimuli and Nf is the total number of endplate potentials failure as described in Martin, R. R., *Physiol. Rev.*, 1966, 46:51-66. The phrenic nerve was stimulated at 0.5 Hz. Miniature endplate amplitudes were corrected assuming a $-80$ mV membrane potential and their frequency of appearance counted over 0.5 to 3 minutes. The Levator auris muscle, described in Angaut-Petit et al., *Neuro. Sci. Letr.*, 1987, 82:83-88, as used to study the presynaptic motor nerve terminals currents. The presynaptic currents were recorded with glass microelectrodes filled with 2M NaCl of 5 o 15 Mohm resistance placed inside the perineural sheath of small nerve branches near the endplate areas described by Mallori, *J. Physiol. (London)*, 1985, 363:565-575; and Penner et al., *Pflugers Arch*, 1986, 806:190-193. The nerves were stimulated using suction electrodes coupled to a pulse generator with associated stimulus isolation unit (0.1 msec). The recording microelectrodes were connected to an Axoclamp 1B amplifier. The signals were digitized (Tecmar labmaster A/D converter), stored and analyzed by a computer.

B. Electrophysiology

1. Presynaptic Currents

Nerve muscle preparations were incubated in normal ringer plus curare, 30 μM, tetraethyl ammonium 10 mM, 3-4, diaminopyridine 250 μM, and procane 100 μM. Presynaptic current was recorded (FIG. 8, trace a). 300 μM of compound S was added to the solution, and presynaptic current was measured (FIG. 8, trace b).

Figure 8:
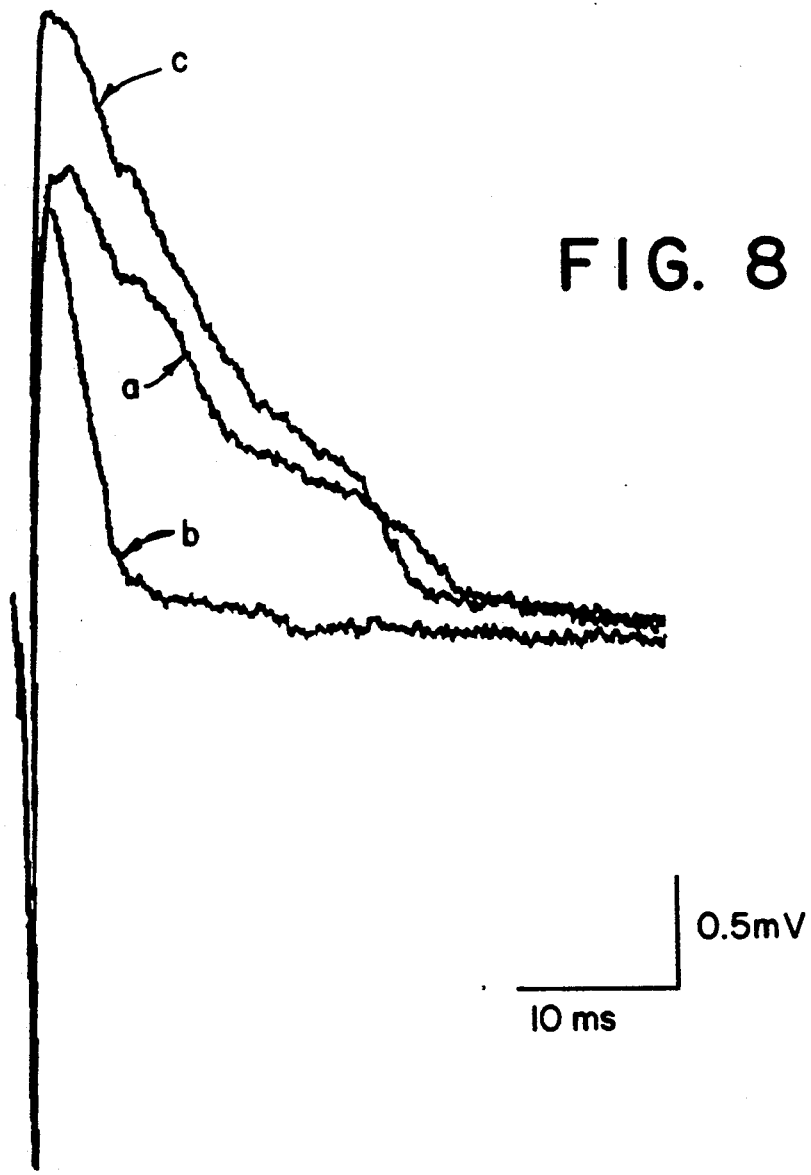
FIG. 8 is a superimposition of traces of perineural presynaptic currents in nerve muscle preparations before (a) and after (B) the addition of 300 μM of compound S. In (c) calcium concentration was raised in the presence of compound S.

Calcium content was increased to 6 mM in the presence of Compound S, and presynaptic current was measured (FIG. 8, trace c).

Submillimolar concentrations of compound S were also effective in blocking the slow long lasting $Ca^{2+}$ component of the presynaptic currents. The blocking effect of the toxin was overcome by increasing the calcium concentration in the bath solution in a manner similar to that for other divalent cations as reported by Lin et al., *Proc. Nat'l Acad. Sci. USA*, 1990, 87:4538-4542.

2. Transmitter Release a. Compound S

Synthetic arginine-polyamine (spermidine) adducts were found to have FTX-like activity. Quantal content of transmitter release was inhibited in a dose dependent manner with low (millimolar) concentrations of Compound S.

B. Comparative Data

The inhibitory action of FTX on synaptic transmission was further characterized by studying the effect of different concentrations of FTX on quantal content of evoked release. The muscles were incubated in a low $Ca^{2+}$/high Mg solution. The control m values were between 2.1 and 3.8. A 50% inhibition of the quantal content of evoked release was obtained with submicromolar concentration of FTX.

In contrast, evoked neuromuscular transmission was completely insensitive to omega-conotoxin (5 uM) tested under similar conditions as described by Protti et al., *Brain Res.*, 1991, 557:336-339.

3. Spontaneous Transmitter Release a. Compound S

Spontaneous transmitter release was also affected by Compound S. A 50 to 100% increase in miniature frequency was observed in muscles treated with 0.5 ul/ml of purified toxin or with 1 mM of Compound S. The amplitude of the miniature endplate potentials was substantially reduced (over 40%) without major alterations in their time course.

Compound S exhibits high potency in blocking synaptic transmission and presynaptic $Ca^{2+}$ currents at the mouse neuromuscular junction, as does FTX. However, Compound S can be readily synthesized and characterized and is therefore readily available.

4. Further Comparative Data

Hemidiaphragms incubated in normal Ringer were treated with 1 ul/ml of FTX. After a few minutes muscle contraction elicited by nerve stimulation was abolished. Intracellular recording showed that nerve stimulation failed to trigger transmitter release in a high percentage of trails. When transmitter release was evoked, small endplate potentials were recorded with fluctuating amplitude multiples of the miniature endplate potential amplitude. Neuromuscular transmission and contraction was restored a few minutes after washing the preparation with normal solution.

EXAMPLE 9 POTASSIUM CHANNEL ACTIVITY BASED ON PURIFIED AXON MEMBRANE

A. Membrane Fractionation

Myelin, periaxolemmal and axolemmal enriched fractions were purified from rat lower brain stem dissected free of visible grey matter. These membrane fractions were all isolated from the same preparation by a modification of the procedure of Detskey et al., *Neurochem. Res.*, 1988, 13:449-454, originally formulated for the isolation of crude axolemmal enriched fractions. The modifications include the use of HEPES instead of TES buffer, the initial centrifugation step was i 0.9M sucrose (BRL, Gaithersberg, Md.) rather than 1.0M and that after the first centrifugation step the floated membranes were rehomogenized in 0.85M sucrose and recentrifuged. The resultant floating membrane pads were washed in 10 mM HEPES pH 7.4 containing 5 mM EDTA. The membranes were then osmotically shocked in this buffer for 1.5 hours. The overnight discontinuous density gradient centrifugation step described in the original procedure was carried out on a gradient of 15, 24, 28, 32 and 37% sucrose. The sucrose concentrations were defined by density determined using a refractometer (Fisher Scientific, Pittsburgh, Pa.).

The myelin, sedimenting on the 15-24% sucrose interface, and crude axolemma, sedimenting at the 28-32% sucrose interface, isolated by this procedure were purified further. The myelin was osmotically shocked with distilled water and sedimented twice at 12,000×g in a Beckman Instruments (Wakefield, Mass.) Model J2-21 centrifuge to remove residual microsomal contaminants and layered over 0.75M sucrose. The material was centrifuged in a SW-28 rotor at 75,000×g for 1.5 hours in a Beckman L7-55 ultracentrifuge. The band floating on 0.75M sucrose was taken as purified myelin.

The axolemmal subfractions were purified from crude axolemma after its lysis for 30 minutes in 5 mM Tris-HCl, pH 8.3, containing 0.1Mm EDTA. The lysate was made isotonic by the addition of ¼ volume of 40% sucrose and was layered over 0.65M, 0.8M and 1.0M sucrose and centrifuged at 75,000×g for 1.5 hours. Since most myelin fractions have densities less than 0.65M this step was included to preclude residual myelin contaminants, although usually little material was observed on this layer. The material on the 0.8M and 1.0M sucrose layers were defined as the 0.8M and 1.0M subfractions. These membranes were diluted in deionized water and centrifuged at 15,000×g for 20 minutes to remove any small membrane contaminants. The extrinsic membrane proteins of these fractions were identified by treatment of the membranes with $Na_2CO_3$, as described in Sapirstein et al., *J. Neurochem.*, 1988, 51(3):925-933, and the extracted proteins precipitated with 10% cold trichloroacetic acid.

B. Electrophysiology

The initial homogenate contained 5 mM β mercaptoethanol to retain active ion channels. Electrophysiologic analysis of ion channel activity was carried out by the fusion of membrane subfractions. Membranes were resuspended into 400 mM sucrose using a polytron for 15 seconds to form osmotically-loaded vesicles for fusion to the bilayer with lipid bilayers coating the surface of glass pipettes, as described by Llinas et al., *Proc. Nat'l Acad. Sci. USA*, 1989, 86:1689-1693. The final concentration of the membrane subfractions on the cis side of the bilayer was approximately 13 ug/ml. Micropipettes with a tip diameter of approximately 1 micron (Corning 7052 glass, Corning, N.Y.) were pulled using a Kopf Model 720 Electrode Puller (Tujunga, Calif.). Lipid bilayers were formed using a 1:1 mixture of phosphatidyl ethanolamine and phosphatidyl serine (Sigma Chem. Co., St. Louis, Mo.) using the "tip-dip" technique of Coronado and Latorre as described in *Biophysical Jour.*, 1983, 43:231-236. Voltages were applied via an Axon Instruments (Foster City, Calif.) A12120 patch-clamp amplifier with a 100 GOhm head stage. The bathing solution was held at ground The data obtained in the channel studies were amplified to 100 Mv/pA and the membrane current was recorded on a Neurocorder DR-384 (NeuroData, New York) for subsequent analysis. The data were filtered at 1 kHz and digitized at a rate of 25,000 samples/sec. The digitized records wee then analyzed by computer using the pClamp program (Axon Instruments). Experiments were performed using symmetrical bathing solutions of 150 l mM of KCl (for $K^+$ conductances). Channel conductances are determined as pico-siemans (pS), calculated as pS=pA/V.

Results are illustrated in FIGS. 9A, B, C, and D.

Axolemma membrane vesicles were added to the outside bathing solution and were allowed to fuse with the lipid bilayer. Channel-like activity was measured at different holding potentials. After determining a control value (FIG. 9A). compound (ZZ) at a concentration of 1 mM was added to the bathing solution. Channel-like activity as monitored by the application of 50 mV/msec at one (FIG. 9B) and three (FIG. 9C) minute intervals after the addition of compound (ZZ). Channel-like activity was monitored by the application of 75 mV/msec at a three-minute interval (FIG. 9D) after the addition of compound (ZZ).

At this concentration, compound (ZZ) was fond to abolish potassium channel activity in this membrane within three minutes.

EXAMPLE 10 SODIUM CHANNEL ACTIVITY BASED ON PURIFIED AXON MEMBRANE

The procedure of Example 9 is followed. However, $Na^+$ channel analysis is performed. $Na^+$ channel analyses are performed by extending channel open times by the addition of batrachotoxin (BTA) (Laboratory of Bioorganic Chemistry, NIDDK, Bethesda, Md) at the final concentration of 120 nM, along with the membrane vesicles, to the cis side of the bilayer as described by O'Leary et al., *Mol. Pharmacology*, 1989, 36:789-795.

Figure 10:
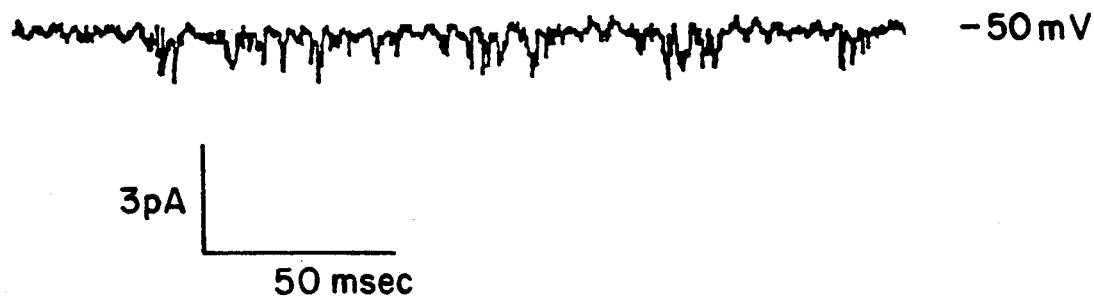
FIG. 10 is a trace of the sodium channel activity in purified axon membrane to which a 50 mV/1 msec voltage is applied, prior to the addition of any compound according to the present invention.

After determining a control value (FIG. 10), compound (ZZ) at a concentration of 1 mM is added to the bating solution. Channel-like activity is monitored, and $Na^+$ channel activity in this membrane is abolished.

What is claimed is:

1. A method for regulating calcium transport across cellular membranes possessing calcium channels comprising exposing a cell membrane possessing said channels to the presence of at least one non-aromatic polyamine compound of the formula:

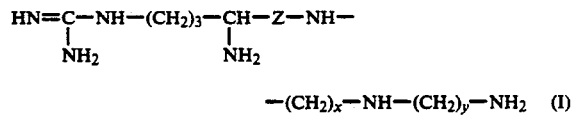

$$-(CH_2)_x-NH-(CH_2)_y-NH_2 \quad (I)$$

wherein x and y are integers independently selected from 3 or 4 and wherein Z is a carbonyl, $CH_2$, or single bond; said polyamine being present in an amount effective to block conductance of said channel without having a substantial direct effect on the conductance of other ions.

2. The method of claim 1 wherein said calcium channels are P-channels.
3. The method of claim 1 wherein both x and y are 3.
4. The method of claim 1 wherein x is 4 and y is 3.
5. The method of claim 1 wherein said polyamine is a mixture of two polyamines according to said formula, the first polyamine having x=4 and y=3 and the second polyamine having x=3 and y=4.
6. The method of claim 1 wherein x, y=3 and Z=CO.
7. A compound of the formula:

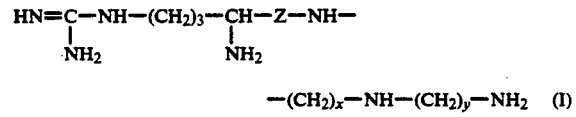

$$-(CH_2)_x-NH-(CH_2)_y-NH_2 \quad (I)$$

wherein x, y are integers independently selected from 3 or 4 and wherein Z is carbonyl, $CH_2$, or a single bond.

8. The compound of claim 7 wherein x, y=3 and Z is carbonyl.
9. The compound of claim 7 wherein x, y=3 and Z is a single bond.
10. The compound of claim 7 wherein x=3, y=4 and Z=CO.
11. The compound of claim 7 wherein x=4, y=3 and Z=CO.
12. A compound of the formula:

wherein n is an integer between 6 and 12 inclusive, R is HN=C(NH$_2$—NH—(CH$_2$)$_3$—CH(NH$_2$) and Z is selected from the group consisting of CO, CH$_2$, or a single bond.

13. The compound of claim 12 wherein Z=CH$_2$ and n=6.

14. The compound of claim 12 wherein Z=CH$_2$ and n=8.

15. The compound of claim 12 wherein Z=CH$_2$ and n=12.

16. A method for regulating potassium transport across cellular membranes possessing potassium channels comprising exposing a membrane possessing said channels to the presence of at least one compound of the formula:

$$R-Z-NH-(CH_2)_n-NH_2$$

wherein n is an integer between 6 and 12 inclusive, R is HN=C(NH$_2$)—NH—(CH$_2$)$_3$—CH(NH$_2$) and Z is selected from the group consisting of CO, CH$_2$, or a single bond;

said compound being present in an amount effective to block conductance of said channels.

17. The method of claim 16 wherein Z=CH$_2$.

18. The method of claim 16 wherein Z=CH$_2$ and n=10.

19. A compound of the formula:

$$R-Z-NH-(CH_2)_x-NH-(CH_2)_y-NH_2 \qquad (III)$$

wherein R is [H$_2$N—(CH$_2$)$_4$—CH(NH$_2$) or HN=C(NH$_2$D)—NH—(CH$_2$-)$_5$—CH(NH$_2$)]HN=C(NH$_2$)—NH—(CH$_2$-)$_3$—CH(NH$_2$);

Z is carbonyl, CH$_2$ or a single bond; and x, y are integers independently selected from 3 or 4.

20. A compound of the formula:

$$HN=C-NH-(CH_2)_3-CO-NH(CH_2)_m-(NH)_t-(CH_2)_l-NH_2 \qquad (IV)$$
$$\phantom{HN=C}|$$
$$\phantom{HN=C}NH_2$$

wherein t is zero or 1;

l is 3 or 4; and m is 3 or 4 when t is 1 and m is zero when t is zero.

21. The compound of claim 20 wherein t and m are zero.

22. The compound of claim 20 wherein t is 1 and n, m are 3.

23. A method for regulating sodium conductance in cell membranes possessing sodium channels comprising exposing a cell membrane possessing said channels to the presence of a compound of the formula:

$$HN=C-NH-(CH_2)_3-CO-NH(CH_2)_m-(NH)_t-(CH_2)_l-NH_2$$
$$\phantom{HN=C}|$$
$$\phantom{HN=C}NH_2$$

wherein t is zero or 1;

l is 3 or 4; and m is 3 or 4 when t is 1 and m is zero when t is zero;

said compound being present in an amount sufficient to block conductance of said channels.

* * * * *